(12) United States Patent
Zhang et al.

(10) Patent No.: US 11,241,376 B2
(45) Date of Patent: Feb. 8, 2022

(54) SKINCARE COMPOSITION CONTAINING PLANT EXTRACTS AND PREPARATION METHOD THEREOF

(71) Applicant: ZHEJIANG KANGMANJIA DAILY NECESSITIES CO., LTD, Jinhua (CN)

(72) Inventors: Xunting Zhang, Jinhua (CN); Weifang Zhong, Jinhua (CN)

( * ) Notice: Subject to any disclaimer, the term of this patent is extended or adjusted under 35 U.S.C. 154(b) by 95 days.

(21) Appl. No.: 16/916,204

(22) Filed: Jun. 30, 2020

(65) Prior Publication Data

US 2021/0007966 A1 Jan. 14, 2021

Related U.S. Application Data

(63) Continuation-in-part of application No. PCT/CN2019/121335, filed on Nov. 27, 2019.

(30) Foreign Application Priority Data

Jul. 11, 2019 (CN) .......................... 201910622832.X

(51) Int. Cl.
| | |
|---|---|
| *A61K 8/97* | (2017.01) |
| *A61K 8/60* | (2006.01) |
| *A61K 8/34* | (2006.01) |
| *A61K 8/73* | (2006.01) |
| *A61Q 19/00* | (2006.01) |

(52) U.S. Cl.
CPC .............. *A61K 8/97* (2013.01); *A61K 8/342* (2013.01); *A61K 8/602* (2013.01); *A61K 8/73* (2013.01); *A61Q 19/00* (2013.01); *A61K 2800/10* (2013.01); *A61K 2800/48* (2013.01); *A61K 2800/591* (2013.01); *A61K 2800/85* (2013.01)

(58) Field of Classification Search
None
See application file for complete search history.

(56) References Cited

U.S. PATENT DOCUMENTS

2009/0280150 A1* 11/2009 Kamen ................ A45D 44/002
424/401

FOREIGN PATENT DOCUMENTS

| CN | 109453087 A | 3/2019 |
|---|---|---|
| CN | 109602668 A | 4/2019 |

OTHER PUBLICATIONS

Skin barrier effect and measurement on xylityigiucoside humectant, LIANG Xiao-yu, Jun. 30, 2012.

* cited by examiner

*Primary Examiner* — Dominic Lazaro
(74) *Attorney, Agent, or Firm* — Rumit Ranjit Kanakia

(57) ABSTRACT

A skincare composition containing plant extracts and a preparation method thereof. The skincare composition containing plant extracts, comprising, by weight percentage, the following components: 0.2-0.5% of a complex plant extract, 1-3.5% of a carbohydrate derivative, 50-60% of a thickener, 1.5-4% of a first skin conditioner, 0.1-0.3% of a second skin conditioner, 2-3% of a third skin conditioner, 3-5% of a first moisturizer, 4-6% of a second moisturizer, and the balance of deionized water.

7 Claims, No Drawings

SKINCARE COMPOSITION CONTAINING PLANT EXTRACTS AND PREPARATION METHOD THEREOF

TECHNICAL FIELD

The present application belongs to the field of skincare products, and in particular relates to a skincare composition containing plant extracts and a preparation method thereof.

BACKGROUND

In recent years, with the change of climate and environment, the skin is more prone to hurt, so the demand and requirements for skincare products are getting higher and higher.

At present, skincare products containing plant active ingredients are favored by consumers because of their mild effects, less side effects, and easy absorption. For example, *Matricaria recutita*, which has significant antioxidant capacity and can enhance the skin's moisturizing ability, prevent dry skin and enhance skin barrier function, is widely applied to sensitive skin. The extract of *Pleurotus citrinopileatus* is rich in various small-molecule functional ingredients such as erythrothioneine. These substances can effectively penetrate into skin cells, and are fully absorbed and utilized by cells, which can nourish the skin, eliminate free radicals, inhibit tyrosinase and achieve other physiological functions.

However, the plant active ingredients are complex, improper use of them will not only cause waste of resources, but also may cause skin problems such as clogged skin pores, hair follicle inflammation, large pores, blackheads, and the skincare products currently available on the market have simple effects, and have to use multiple different skincare products to solve the skin problems. For example: CN105232443A discloses a lotion only having an anti-allergic effect, composed of glycerin, corn propylene glycol, leuconostoc/radish root fermentation product filtrate, *Hydrocotyle asiatica* extract, *Polygonum cuspidatum* root extract, *Scutellaria* extract, tea extract, *Chamomilla recutita* extract, *Rosmarinus officinalis* leaf extract and *Hamamelis virginiana* flower water; CN109199962A discloses a cosmetic only having an acne removing effect, composed of Portulaca oleracea extract, kava extract, *Hydrocotyle asiatica* extract, *Polygonum cuspidatum* root extract, *Scutellaria* root extract, green tea extract, *Glycyrrhiza glabra* root extract, *Chamomilla recutita* extract and *Rosmarinus officinalis* extract.

Therefore, the development of a skincare product that efficiently utilizes plant active ingredients and has multiple functions is desired to meet the increasing demand for use.

SUMMARY

In order to solve the above technical problems, the first aspect of the present application provides a skincare composition containing plant extracts, comprising, by weight percentage, the following components: 0.2-0.5% of a complex plant extract, 1-3.5% of a carbohydrate derivative, 50-60% of a thickener, 1.5-4% of a first skin conditioner, 0.1-0.3% of a second skin conditioner, 2-3% of a third skin conditioner, 3-5% of a first moisturizer, 4-6% of a second moisturizer, and the balance of deionized water.

Further, the complex plant extract comprises one or more of *Hydrocotyle asiatica* extract, *Polygonum cuspidatum* root extract, *Dendrobium nobile* extract, *Scutellaria* root extract, tea extract, *Glycyrrhiza glabra* root extract, *Sophora flavescens* root extract, *Chamomilla recutita* extract and *Rosmarinus officinalis* leaf extract.

Further, the carbohydrate derivative is one or more of glycosylglycerol, xylitylglucoside, anhydroxylitol, fructose, and xylitol.

Further, the thickener is one or more of lubrajel, cetostearyl alcohol, xanthan gum, and Carbomer.

Further, the first skin conditioner is an energy factor and/or a hibiscus sabdariffa flower extract; the second skin conditioner is one or more of carnosine, squalene, and tocopherol; the third skin conditioner is a chlorella extract and/or a red ginseng fermentation broth.

Further, the energy factor is one or more of artemia extract, palmitoyl tripeptide-1, palmitoyl tetrapeptide-7, and palmitoyl pentapeptide-4; the mass ratio of the energy factor to the carbohydrate derivative is (0.5-3): 2.

Further, the mass ratio of the energy factor to the carbohydrate derivative is 1:2.

Further, the mass ratio of the red ginseng fermentation broth to the carbohydrate derivative to the complex plant extract is (1.3-2):(1-3.5):(0.2-0.5).

The second aspect of the present application provides a preparation method of the skincare composition, at least comprising the following steps:

(1) adding a thickener and deionized water to a pot and stirring uniformly to obtain a mixture denoted as Phase A; adding a second moisturizer and a second skin conditioner to a pot and stirring uniformly to obtain a mixture denoted as Phase B; adding a first skin conditioner and a first moisturizer to a pot and stirring uniformly to obtain a mixture denoted as Phase C; and adding a complex plant extract, a carbohydrate derivative, and a third skin conditioner to a pot and stirring uniformly to obtain a mixture denoted as Phase D;

(2) adding Phase A to a pot, stirring to uniformly dissolve Phase A, and then vacuuming and stirring;

(3) adding Phase B to the pot of step (2) and vacuuming and stirring uniformly; and (4) adding Phase C and Phase D to the pot of the step (3) in sequence, and further vacuuming and stirring uniformly, and then discharging.

Further, in the steps (2), (3), and (4), the vacuum degree of the pot ranges from −0.08 MPa to −0.01 MPa.

The present application further provides an essence lotion prepared from the above skincare composition.

The present application has the beneficial effects of providing a skincare composition containing plant extracts and a preparation method thereof; the product can quickly penetrate into skin tissue, promote absorption of active ingredients, is capable of repairing damaged skin, and also has anti-wrinkle, anti-aging, whitening, moisturizing, and anti-allergy effects, thus being suitable for people of all types of sensitive skin.

DETAILED DESCRIPTION OF THE EMBODIMENTS

The content of the present invention can be further understood in conjunction with the following detailed description of the preferred embodiments of the invention and the accompanying embodiments. All technical and scientific terms used herein have the same meaning as commonly understood by one of ordinary skill in the art to which this invention belongs, unless otherwise indicated. If the definition of a specific term disclosed in the prior art is inconsistent with any of the definitions provided in the present application, the definition of the term provided in the present application shall prevail.

The use of features not specified in the singular and plural forms are also intended to include features in the plural form, unless the context clearly indicates otherwise. It will also be understood that the term "prepared from" is used synonymously with "comprise", terms "include", "including", "having", "comprising" and/or "comprising", as used in the present specification, indicate a stated composition, step, method, article or device, but does not exclude the presence or addition of one or more other compositions, steps, methods, articles or devices. Moreover, when describing embodiments of the present application, the use of "preferred", "preferably", "more preferred" and the like refers to embodiments of the invention that may provide certain benefits in some instances. However, other embodiments may also be preferred under the same circumstances or in other circumstances. In addition, the recitation of one or more preferred embodiments does not imply that other embodiments are not available, and is not intended to exclude other embodiments from the scope of the invention.

In order to solve the above technical problems, the first aspect of the present application provides a skincare composition containing plant extracts, comprising, by weight percentage, the following components: 0.2-0.5% of a complex plant extract, 1-3.5% of a carbohydrate derivative, 50-60% of a thickener, 1.5-4% of a first skin conditioner, 0.1-0.3% of a second skin conditioner, 2-3% of a third skin conditioner, 3-5% of a first moisturizer, 4-6% of a second moisturizer, and the balance of deionized water.

Complex Plant Extract

The complex plant extract is a product formed by extracting active ingredients in different plants by technical means without changing the structure of the active ingredients. Products with different functions are formed according to different plant species.

In some preferred embodiments, the complex plant extract comprises one or more of *Hydrocotyle asiatica* extract, *Polygonum cuspidatum* root extract, *Dendrobium nobile* extract, *Scutellaria* root extract, tea extract, *Glycyrrhiza glabra* root extract, *Sophora flavescens* root extract, *Chamomilla recutita* extract and *Rosmarinus officinalis* leaf extract.

Further preferably, the complex plant extract comprises *Hydrocotyle asiatica* extract, *Polygonum cuspidatum* root extract, *Scutellaria* root extract, tea extract, *Glycyrrhiza glabra* root extract, *Chamomilla recutita* extract and *Rosmarinus officinalis* leaf extract.

More preferably, the complex plant extract comprises *Hydrocotyle asiatica* extract, *Polygonum cuspidatum* root extract, *Scutellaria* root extract, tea extract, *Glycyrrhiza glabra* root extract, *Chamomilla recutita* extract and rosemary leaf extract, and is commercially available from Shanghai Ruimu Chemical Co., Ltd., with the brand name of Calm Young.

The complex plant extract in the embodiments of the present application, under the interaction of components such as resveratrol, emodin, glycosides, flavonoids, and essential oils, is contributive to inhibiting the expression of inflammatory factors in skin tissues and preventing various types of sensitive skin from being allergic to skincare products. Moreover, the active ingredients in the complex plant extract, mainly including proteins and saccharides similar to those of the human body, have mild effects, and will not produce a violent effect on the cell tissue of the skin to cause redness, allergies, etc., thus achieving the anti-allergic, anti-inflammatory and sedative effects. Moreover, after being absorbed by the cell tissue, the above components are capable of improving blood circulation, balancing the secretion of oil by the sebaceous glands, and improving the state of the skin. However, since the active ingredients in the complex plant extract are complicated and take effect slowly, it takes a long time to see a remarkable effect, and the skin state does not change significantly in a short time. Especially for some oily skin, because the sebaceous glands secrete the oil faster, it is easy to cause the pores to be clogged by the oil, which affects the penetration of the composition into the skin; even under the action of various oil components, the complex plant extract may also clogs the pores, which in turn causes inflammation of the hair follicles, causing problems such as large pores and blackheads.

Carbohydrate Derivative

The carbohydrate derivative is a composite compounded from a plurality of sugar alcohols and glycosides and is mainly used for moisturizing action in the present application.

In some preferred embodiments, the carbohydrate derivative is one or more of glycosylglycerol, xylitylglucoside, anhydroxylitol, fructose, and xylitol.

Further preferably, the carbohydrate derivative comprises glycosylglycerol, xylitylglucoside, anhydroxylitol, fructose, and xylitol.

Further preferably, the carbohydrate derivative in embodiments of the present application comprises glycosylglycerol, xylitylglucoside, anhydroxylitol, fructose, and xylitol, and is commercially available from Shanghai Fine Chemical Industrial Co., Ltd., under the brand name of C-MOIST.

The carbohydrate derivative in the embodiments of the present application has good affinity to water and oil due to the special structure of the component, and can activate capillary pores to absorb and maintain moisture in the endothelium, and can really achieve deep hydrating and moisturizing effect especially when used together with sodium hyaluronate, hydrolyzed glycosaminoglycan, etc.

Thickener

Thickeners, also known as gelling agents, are mostly water-soluble polymer compounds that form a three-dimensional crosslinked network structure in water, thereby increasing the viscosity of the cosmetics and increasing the stability of the cosmetics.

In some preferred embodiments, the thickener is one or more of lubrajel, cetostearyl alcohol, xanthan gum, and Carbomer.

Further preferably, the thickener is lubrajel.

Further preferably, the lubrajel in the embodiments of the present application is a composition composed of glycerin, glycerin acrylate/acrylic acid copolymer, phenoxyethanol, and water, and is commercially available from Shanghai Zhaoxin Chemical Co., Ltd., under the brand name of SJgel MSF.

Skin Conditioner

Skin conditioners refer to ingredients that can easily penetrate into the skin and can repair and condition the skin. The skin conditioners have the whitening, anti-wrinkle, redness removing and anti-allergic functions and can improve skin resistance.

The skin conditioners of the present application are divided into a first skin conditioner, a second skin conditioner, and a third skin conditioner.

In some preferred embodiments, the first skin conditioner is an energy factor and/or a hibiscus sabdariffa flower extract.

Further preferably, the first skin conditioner consists of an energy factor and a hibiscus sabdariffa flower extract.

Further preferably, the mass ratio of the energy factor to the hibiscus sabdariffa flower extract is 1:(1-2.5).

Most preferably, the mass ratio of the energy factor to the hibiscus sabdariffa flower extract is 1:2.

In some preferred embodiments, the energy factor is one or more of artemia extract, palmitoyl tripeptide-1, palmitoyl tetrapeptide-7, and palmitoyl pentapeptide-4.

Further preferably, the energy factor consists of artemia extract, palmitoyl tripeptide-1, palmitoyl tetrapeptide-7, and palmitoyl pentapeptide-4.

In some preferred embodiments, the hibiscus sabdariffa flower extract is a lactobacillus/hibiscus sabdariffa flower fermentation product filtrate and/or butanediol.

Further preferably, the hibiscus sabdariffa flower extract consists of a lactobacillus/hibiscus sabdariffa flower fermentation product filtrate and butanediol.

In some preferred embodiments, the mass ratio of the energy factor to the carbohydrate derivative is (0.5-3):2.

Further preferably, the mass ratio of the energy factor to the carbohydrate derivative is 1:2.

By adding a certain amount of the energy factor containing the composite polypeptide to the skincare composition, it is found that the skincare composition is contributive to conditioning the skin and reducing the allergy and irritation of the composition to oily skin and sensitive skin. It is also found that, when the mass ratio of the energy factor to the carbohydrate derivative is 1:2, its conditioning effect on the skin is most remarkable and rapid. It may be because the carbohydrate derivative helps to clean the pores quickly, and absorbs water to moisturize the skin, while driving and accelerating the penetration of energy factors into the skin and the absorption of energy factors by the skin cells; and under the action of the carbohydrate derivative, the formation of cellular interleukin and other components can be effectively delayed and inhibited, thereby avoiding unnecessary inflammatory reactions and glycosylation damage.

In some preferred embodiments, the second skin conditioner is one or more of carnosine, squalene, and tocopherol.

Further preferably, the second skin conditioner is carnosine.

In some preferred embodiments, the third skin conditioner is a chlorella extract and/or a red ginseng fermentation broth.

Further preferably, the third skin conditioner consists of a chlorella extract and/or a red ginseng fermentation broth.

More preferably, the mass ration of the chlorella extract to the red ginseng fermentation broth is 1:2.

Still more preferably, the red ginseng fermentation broth is a lactobacillus/ginseng root fermentation product filtrate.

The Red ginseng fermentation broth comprises a large number of small-molecular protein fermentation products, which can quickly penetrate into skin cells, can whiten and brighten skin in a short time, promote cell regeneration, and make skin have good elasticity.

In some preferred embodiments, the mass ratio of the red ginseng fermentation broth to the carbohydrate derivative to the complex plant extract is (1.3-2):(1-3.5):(0.2-0.5).

Further preferably, the mass ratio of the red ginseng fermentation broth to the carbohydrate derivative to the complex plant extract is 2:2:0.3.

Further preferably, the energy factor in the embodiments of the present application consists of artemia extract, palmitoyl tripeptide-1, palmitoyl tetrapeptide-7, and palmitoyl pentapeptide-4, and is commercially available from Shanghai Yutong Biotechnology Co., Ltd.; the hibiscus sabdariffa flower extract in the embodiments of the present application consists of a lactobacillus/hibiscus sabdariffa flower fermentation product filtrate and butanediol, and is commercially available from Haiyanzhen Industrial Co., Ltd.; the carnosine in the embodiments of the present application is commercially available from Shanghai Reshy Industrial Co., Ltd.; the chlorella extract in the embodiments of the present application is commercially available from Shanghai Ruimu Chemical Co., Ltd., under the brand name of KBGA; the red ginseng fermentation broth in the embodiments of the present application is lactobacillus/ginseng root fermentation product filtrate and is commercially available from Shanghai Ourong Biological Technology Co., Ltd., under the brand name of KRG anti.

It is found that when the mass ratio of the red ginseng fermentation broth to the carbohydrate derivative to the complex plant extract is (1.3-2):(1-3.5):(0.2-0.5), the stability of the composition is remarkably improved, and the skin oil of oily skin and sensitive skin can also be adjusted and balanced significantly. It may be because the water-absorbing and moisturizing effect of the carbohydrate derivative helps to clean the pores, remove the dirt and oily fat out of the pores, promote the penetration and absorption of ingredients such as the red ginseng fermentation broth, and thus helps to regulate the abnormal secretion of the sebaceous glands. Moreover, due to having mild effects, the complex plant extract can avoid the stress response of sensitive skin to the red ginseng fermentation broth, the energy factor and other ingredients; in addition, the penetration and absorption of the complex plant extract into skin can be improved under the action of the carbohydrate derivative, the red ginseng fermentation broth and other ingredients, avoiding a large amount of the complex plant extract remaining in the pores, clogging the pores, causing inflammation of the hair follicles and redness, and further causing skin problems of pimples and acnes due to abnormal oil secretion of hair follicles and breeding of acarid.

Moisturizer

Moisturizers, mostly hydrophilic moisturizing substances, can bring water molecules in cosmetics into the skin for instant hydration, and also can absorb moisture in the air to achieve a long-lasting moisturizing effect, so that the skin maintains a good water balance state and skin dryness is relieved.

The moisturizers in the present application are classified into a first moisturizer and a second moisturizer.

In some preferred embodiments, the first moisturizer is one or more of moisturizer 301, moisturizer 886, glycerin, and panthenol.

Further preferably, the first moisturizer consists of moisturizer 301 and moisturizer 886.

More preferably, the mass ratio of the moisturizer 301 and the moisturizer 886 is 1:1.

In some preferred embodiments, the second moisturizer is one or more of PHL, hydrolyzed glycosaminoglycan, and methylpropanediol.

Further preferably, the second moisturizer consists of PHL and methylpropanediol.

More preferably, the mass ratio of the PHL to the methylpropanediol is 1:4.

Most preferably, the moisturizer 301 in the embodiments of the present application is composed of sodium hyaluronate, sodium polyglutamate, tremella polysaccharide, 1,2-hexanediol, caprylhydroxamic acid, and butanediol, and is commercially available from Shanghai Yi-Ye Biological Technology Co., Ltd., under the brand name of Yi-301. The moisturizer 886 in the embodiments of the present application consists of water, butanediol, sodium polyglutamate, sodium hyaluronate, caesalpinia spinosa gum, xylitol, and dsuccinoglycan, and is commercially available from Shanghai Fine Chemical Industrial Co., Ltd., under the brand of moisturizer 886. The PHL in the embodiments of the present application consists of octanoyl hydroxamic acid, 1.2-hexanediol and 1.3-propylene glycol and is commercially available from Shanghai Haoyun Industrial Co., Ltd., under a band name of PHL. Methylpropanediol in the embodiments of the present application is commercially available from Shanghai Lijing Industrial Co., Ltd.

A second aspect of the present application provides a preparation method of the skincare composition, at least comprising the following steps:

(1) adding a thickener and deionized water to a pot and stirring uniformly to obtain a mixture denoted as Phase A; adding a second moisturizer and a second skin conditioner to a pot and stirring uniformly to obtain a mixture denoted as Phase B; adding a first skin conditioner and a first moisturizer to a pot and stirring uniformly to obtain a mixture denoted as Phase C; and adding a complex plant extract, a carbohydrate derivative, and a third skin conditioner to a pot and stirring uniformly to obtain a mixture denoted as Phase D;

(2) adding Phase A to a pot, heating Phase A to 80° C. while slowly stirring at 20 Hz, stirring at 20 Hz to uniformly dissolve Phase A, and stirring for cooling under a vacuum degree of −0.04 MPa;

(3) cooling to 50° C., adding Phase B to the pot of step (2), stirring uniformly at 30 Hz under a vacuum degree of −0.04 MPa, and cooling; and (4) cooling to 40° C., adding Phase C and Phase D to the pot of the step (3) in sequence, and further stirring at 30 Hz under a vacuum degree of −0.04 MPa, and cooling.

The present application further provides an essence lotion prepared from the above skincare composition.

EMBODIMENTS

The technical solutions of the present application are described in detail below by way of embodiments, but the scope of protection of the present application is not limited to the embodiments. Raw materials used in the present application are commercially available unless otherwise stated.

Example 1

Example 1 provided a skincare composition containing plant extracts, comprising, by weight percentage, the following components: 0.3% of a complex plant extract, 2% of a carbohydrate derivative, 55% of a thickener, 3% of a first skin conditioner, 0.2% of a second skin conditioner, 3% of a third skin conditioner, 4% of a first moisturizer, 5% of a second moisturizer, and the balance of water.

The complex plant extract consisted of *Hydrocotyle asiatica* extract, *Polygonum cuspidatum* root extract, *Scutellaria* root extract, tea extract, *Glycyrrhiza glabra* root extract, *Chamomilla recutita* extract and *Rosmarinus officinalis* leaf extract, and was commercially available Shanghai Ruimu Chemical Co., Ltd., under the brand name of Calm Young.

The carbohydrate derivative consisted of glycosylglycerol, xylitylglucoside, anhydroxylitol, fructose, and xylitol, and was commercially available from Shanghai Fine Chemical Industrial Co., Ltd., under the brand name of C-MOIST.

The first skin conditioner consisted of an energy factor and a hibiscus sabdariffa flower extract; the ratio of the energy factor to the hibiscus sabdariffa flower extract here was 1:2.

The energy factor consisted of artemia extract, palmitoyl tripeptide-1, palmitoyl tetrapeptide-7, and palmitoyl pentapeptide-4, and was commercially available from Shanghai Yutong Biotechnology Co., Ltd.

The hibiscus sabdariffa flower extract consisted of a lactobacillus/hibiscus sabdariffa flower fermentation product filtrate and butanediol and was commercially available from Haiyanzhen Industrial Co., Ltd.

The second skin conditioner was carnosine which was commercially available from Shanghai Reshy Industrial Co., Ltd.

The third skin conditioner consisted of a chlorella extract and a red ginseng fermentation broth; the mass ratio of the chlorella extract to the red ginseng fermentation broth was 1:2.

The chlorella extract was commercially available from Shanghai Ruimu Chemical Co., Ltd. under the brand name of KBGA.

The red ginseng fermentation broth was lactobacillus/ginseng root fermentation product filtrate, and was commercially available from Shanghai Ourong Biological Technology Co., Ltd. under the trade name of KRG anti.

The first moisturizer consisted of a moisturizer 301 and a moisturizer 886; the mass ratio of the moisturizer 301 to the moisturizer 886 was 1:1.

The moisturizer 301 consisted of sodium hyaluronate, sodium polyglutamate, tremella polysaccharide, 1,2-hexanediol, caprylhydroxamic acid, and butanediol, and was commercially available from Shanghai Yi-Ye Biological Technology Co., Ltd. under the brand name of Yi-301.

The moisturizer 886 consisted of water, butanediol, sodium polyglutamate, sodium hyaluronate, caesalpinia spinosa gum, xylitol, and succinoglycan, and was commercially available from Shanghai Fine Chemical Industrial Co., Ltd. under the brand name of moisturizer 886.

The second moisturizer consisted of PHL and methylpropanediol; the mass ratio of the PHL to the methylpropanediol was 1:4.

The PHL consisted of caprylhydroxamic acid, 1,2-hexanediol, and 1,3-propanediol, and was commercially available from Shanghai Haoyun Industrial Co., Ltd. under the trade name of PHL.

The methylpropanediol was commercially available from Shanghai Lijing Industrial Co., Ltd.

The preparation method of the skincare composition containing plant extracts comprised the following steps:

(1) adding lubrajel and deionized water to a pot and stirring uniformly to obtain a mixture denoted as Phase A; adding PHL, methylpropanediol and carnosine to a pot and stirring uniformly to obtain a mixture denoted as Phase B; adding moisturizer 301, moisturizer 886, an energy factor and hibiscus sabdariffa flower extract to a pot and stirring uniformly to obtain a mixture denoted as Phase C; and adding a complex plant extract, a carbohydrate derivative, chlorella extract and red ginseng fermentation broth to a pot and stirring uniformly to obtain a mixture denoted as Phase D;

(2) adding Phase A to a pot, heating Phase A to 80° C. while slowly stirring at 20 Hz, stirring at 20 Hz to uniformly dissolve Phase A, and stirring for cooling under a vacuum degree of −0.04 MPa;

(3) cooling to 50° C., adding Phase B to the pot of step (2), stirring uniformly at 30 Hz under a vacuum degree of −0.04 MPa, and cooling; and (4) cooling to 40° C., adding Phase C and Phase D to the pot of the step (3) in sequence, and further stirring at 30 Hz under a vacuum degree of −0.04 MPa, and cooling.

Example 2

Example 2 provided a skincare composition containing plant extracts, comprising, different from Example 1, the following components by weight percentage: 0.2% of a complex plant extract, 1% of a carbohydrate derivative, 50% of a thickener, 1.5% of a first skin conditioner, 0.1% of a second skin conditioner, 2% of a third skin conditioner, 3% of a first moisturizer, 4% of a second moisturizer, and the balance of water.

Further provided in this Example was a preparation of the skincare composition containing plant extracts, comprising the steps similar to those in Example 1.

Example 3

Example 3 provided a skincare composition containing plant extracts, comprising, different from Example 1, the following components by weight percentage: 0.5% of a complex plant extract, 3.5% of a carbohydrate derivative, 60% of a thickener, 4% of a first skin conditioner, 0.3% of a second skin conditioner, 3% of a third skin conditioner, 5% of a first moisturizer, 6% of a second moisturizer, and the balance of water.

Further provided in this Example is a preparation of the skincare composition containing plant extracts, comprising the steps similar to those in Example 1.

Example 4

Example 4 provided a skincare composition containing plant extracts, which differed from Example 1 in that the composition was free of the complex plant extract, and the dose of deionized water in the composition is adjusted accordingly.

Further provided in this Example is a preparation of the skincare composition containing plant extracts, comprising the steps similar to those in Example 1.

Example 5

Example 5 provided a skincare composition containing plant extracts, which differed from Example 1 in that the composition was free of the hibiscus sabdariffa flower extract, and the dose of deionized water in the composition was adjusted accordingly.

Further provided in this Example was a preparation of the skincare composition containing plant extracts, comprising the steps similar to those in Example 1.

Example 6

Example 6 provided a skincare composition containing plant extracts, which differed from Example 1 in that the composition was free of the carbohydrate derivative, and the dose of deionized water in the composition was adjusted accordingly.

Further provided in this example was a preparation of the skincare composition containing plant extracts, comprising the steps similar to those in Example 1.

Example 7

Example 7 provided a skincare composition containing plant extracts, which differed from Example 1 in that the composition was free of the lubrajel, and the dose of deionized water in the composition was adjusted accordingly.

Further provided in this example was a preparation of the skincare composition containing plant extracts, comprising the steps similar to those in Example 1.

Example 8

Example 8 provided a skincare composition containing plant extracts, which differed from Example 1 in that the composition was free of the chlorella extract, and the dose of deionized water in the composition was adjusted accordingly.

Further provided in this example was a preparation of the skincare composition containing plant extracts, comprising the steps similar to those in Example 1.

Example 9

Example 9 provided a skincare composition containing plant extracts, which differed from Example 1 in that the composition was free of the red ginseng fermentation broth, and the dose of deionized water in the composition was adjusted accordingly.

Further provided in this Example was a preparation of the skincare composition containing plant extracts, comprising the steps similar to those in Example 1.

Example 10

Example 10 provided a skincare composition containing plant extracts, which differed from Example 1 in that the composition was free of the lubrajel and the carbohydrate derivative, and the dose of deionized water in the composition was adjusted accordingly.

Further provided in this Example was a preparation of the skincare composition containing plant extracts, comprising the steps similar to those in Example 1.

Example 11

Example 11 provided a skincare composition containing plant extracts, which differed from Example 1 in that the composition comprised 2.3% of the first skin conditioner and 0.3% of the energy factor, and the ratio of the energy factor to the hibiscus sabdariffa flower extract was 0.3:2, and the mass dose of deionized water in the composition was adjusted accordingly.

Further provided in this Example was a preparation of the skincare composition containing plant extracts, comprising the steps similar to those in Example 1.

Example 12

Example 12 provided a skincare composition containing plant extracts, which differed from Example 1 in that the composition comprised 6% of the first skin conditioner and 4% of the energy factor, and the ratio of the energy factor to the hibiscus sabdariffa flower extract was 2:1, and the mass dose of deionized water in the composition was adjusted accordingly.

Further provided in this Example was a preparation of the skincare composition containing plant extracts, comprising the steps similar to those in Example 1.

Example 13

Example 13 provided a skincare composition containing plant extracts, which differed from Example 1 in that the composition was free of the energy factor, and the dose of deionized water in the composition was adjusted accordingly.

Further provided in this Example was a preparation of the skincare composition containing plant extracts, comprising the steps similar to those in Example 1.

Example 14

Example 14 provided a skincare composition containing plant extracts, which differed from Example 1 in that the composition comprised 1.5% of the third skin conditioner and 0.5% of the red ginseng fermentation broth, and the mass ratio of the red ginseng fermentation broth to the chlorella extract was 1:2, and the dose of deionized water in the composition was adjusted accordingly.

Further provided in this example was a preparation of the skincare composition containing plant extracts, comprising the steps similar to those in Example 1.

Example 15

Example 15 provided a skincare composition containing plant extracts, which differed from Example 1 in that the composition comprised 8% of the carbohydrate derivative, and the dose of deionized water in the composition was adjusted accordingly.

Further provided in this Example was a preparation of the skincare composition containing plant extracts, comprising the steps similar to those in Example 1.

Example 16

Example 16 provided a skincare composition containing plant extracts, which differed from Example 1 in that the composition comprised 1.5% of the complex plant extract, and the dose of deionized water in the composition was adjusted accordingly.

Further provided in this example was a preparation of the skincare composition containing plant extracts, comprising the steps similar to those in Example 1.

Example 17

Example 17 provided a skincare composition containing plant extracts, which differed from Example 1 in that the composition was free of the complex plant extract, the carbohydrate derivative the, lubrajel, and the energy factor, and the dose of deionized water in the composition was adjusted accordingly.

Further provided in this Example was a preparation of the skincare composition containing plant extracts, comprising the steps similar to those in Example 1.

Performance Evaluation

The skincare compositions obtained in Examples 1 to 17 were tested in the physicochemical properties, properties, and sensitivity.

1. Physicochemical Property Test

The appearance, pH and relative density of the products are measured; the appearance of the products was measured by a sensory method, and the pH was measured by a pH meter.

The relative density is determined as follows: (1) the mass of a dry empty bottle is weighed by a balance and recorded as m1 (g); (2) the bottle is full filled with a liquid to be tested and then capped; the surface of the bottle is wiped dry with cloth or absorbent paper; and the mass of the bottle is then weighed and recorded as m2 (g); (3) the liquid in the bottle is poured out and the bottle is then cleaned with clear water; (4) the empty bottle is then filled with water and capped and the surface of the bottle is wiped dry; the mass of the bottle is then weighed and recorded as m3 (g); and (5) calculation is performed according to the following equation. The density of the liquid to be measured relative to water is $\rho$ relative=(m2−m1)/(m3−m1); the results obtained by the above test steps are shown in Table 1.

Heat Resistance, Cold Resistance, Centrifugal Performance Tests

Heat resistance test: Samples are placed in an electrothermal incubator with a temperature of $(40\pm1)\,°C$ for 24 hours. After the samples are cooled to room temperature, observe whether the samples become thinner, or are changed in color and hardness, or layered, so as to determine the heat resistance of the samples.

Cold resistance test: Samples are placed in a refrigerator with a temperature of $(-5\text{ to }-10)\,°C.\pm1°C$ for 24 hours. After the samples reach room temperature, observe whether the samples become thinner, or are changed in color and hardness, or layered, so as to determine the cold resistance of the samples.

Centrifugation test: Samples are placed in a centrifuge and tested at a speed of (2000-4000) r/min for 30 min to observe the separation and layering of the samples. The results obtained by the test methods described above are shown in Table 2.

Sensitivity Test

The samples of Examples 1 to 17 are subjected to a skin irritation resistance test.

Test method: (1) proper people are selected to do the patch test, a subject with scars, wounds or excessive hair on skin is not qualified, a subject who have a known history of severe allergies or serious allergies to cosmetics is not qualified either; (2) test products are applied to sensitive parts; (3) skin tolerance evaluation indicators at the test parts: itching, tightness, irritation, redness, dryness.

The indicators are graded as follows: Level 0: no sensitive reaction; Level 1: few red spots, slightly dry, few wrinkles; Level 2: red spots, and serious redness; Level 3: burning in a large area, and broken skin. The results obtained by the test method described above are shown in Table 3.

TABLE 1

| Example | Appearance | pH | Relative density |
| --- | --- | --- | --- |
| Example 1 | No abnormality | 6.6 | 1.03 |
| Example 2 | No abnormality | 6.3 | 1.02 |
| Example 3 | No abnormality | 6.4 | 1.01 |
| Example 4 | No abnormality | 6.0 | 1.02 |
| Example 5 | No abnormality | 6.5 | 0.09 |
| Example 6 | No abnormality | 6.2 | 1.01 |
| Example 7 | Abnormal | 6.2 | 1.01 |
| Example 8 | Abnormal | 6.4 | 1.02 |
| Example 9 | No abnormality | 6.6 | 1.01 |
| Example 10 | Abnormal | 6.4 | 0.99 |
| Example 11 | No abnormality | 6.3 | 1.03 |
| Example 12 | No abnormality | 6.0 | 1.01 |
| Example 13 | No abnormality | 6.2 | 1.03 |
| Example 14 | No abnormality | 6.1 | 1.02 |
| Example 15 | No abnormality | 6.2 | 1.01 |
| Example 16 | No abnormality | 6.6 | 1.03 |
| Example 17 | Abnormal | 6.1 | 0.99 |

TABLE 2

| Example | Heat resistance test | Cold resistance test | Centrifugation test |
|---|---|---|---|
| Example 1 | Stable | Stable | Stable |
| Example 2 | Stable | Stable | Stable |
| Example 3 | Stable | Stable | Stable |
| Example 4 | Stable | Stable | Stable |
| Example 5 | Stable | Stable | Stable |
| Example 6 | Unstable | Stable | Unstable |
| Example 7 | Unstable | Unstable | Unstable |
| Example 8 | Unstable | Stable | Unstable |
| Example 9 | Unstable | Stable | Unstable |
| Example 10 | Unstable | Unstable | Unstable |
| Example 11 | Unstable | Stable | Stable |
| Example 12 | Unstable | Stable | Stable |
| Example 13 | Stable | Stable | Stable |
| Example 14 | Unstable | Stable | Unstable |
| Example 15 | Unstable | Stable | Stable |
| Example 16 | Unstable | Stable | Stable |
| Example 17 | Unstable | Unstable | Unstable |

TABLE 3

| Example | Level |
|---|---|
| Example 1 | 0 |
| Example 2 | 0 |
| Example 3 | 0 |
| Example 4 | 2 |
| Example 5 | 1 |
| Example 6 | 1 |
| Example 7 | 0 |
| Example 8 | 0 |
| Example 9 | 0 |
| Example 10 | 0 |
| Example 11 | 1 |
| Example 12 | 1 |
| Example 13 | 2 |
| Example 14 | 1 |
| Example 15 | 1 |
| Example 16 | 1 |
| Example 17 | 2 |

By comparing Examples 1 to 17, it can be understood that the synergistic effect of the complex plant extract, the carbohydrate derivative, and the hibiscus sabdariffa flower extract can greatly improve the skin elasticity, achieve the anti-wrinkle, moisturizing and anti-aging effects, can fade expression lines and Crow's feet, can also prevent allergies, and thus the composition is suitable for all types of sensitive skin. When the chlorella extract, carnosine, red ginseng fermentation broth and lubrajel are used together, the composition not only can quickly whiten and brighten the skin, improve skin elasticity, inhibit inflammation, but also has good stability in certain environments such as high temperature, so that the composition and its skincare products are not degenerated for a long-time storage. Due to the use of energy factors, the skincare composition is contributive to conditioning the skin and reducing the allergies and irritation of the composition on oily skin and sensitive skin.

It is finally noted that the embodiments mentioned above are merely preferred embodiments of the present invention and not intended to limit the present invention. Any of modifications, equivalent substitutions, improvements, etc. made within the spirit and principle of the present invention shall be covered in the protection scope of the present invention.

What is claimed is:

1. A skincare composition containing plant extracts, comprising, by weight percentage, the following components: 0.2-0.5% of a complex plant extract, 1-3.5% of a carbohydrate derivative, 50-60% of a thickener, 1.5-4% of a first skin conditioner, 0.1-0.3% of a second skin conditioner, 2-3% of a third skin conditioner, 3-5% of a first moisturizer, 4-6% of a second moisturizer, and the balance of deionized water, wherein the first skin conditioner is an energy factor and/or a hibiscus sabdariffa flower extract; the second skin conditioner is one or more selected from the group consisting of carnosine, squalene, and tocopherol; the third skin conditioner is a chlorella extract and/or a red ginseng fermentation broth.

2. The skincare composition according to claim 1, wherein the complex plant extract comprises one or more selected from the group consisting of *Hydrocotyle asiatica* extract, *Polygonum cuspidatum* root extract, *Dendrobium nobile* extract, *Scutellaria* root extract, tea extract, *Glycyrrhiza glabra* root extract, *Sophora flavescens* root extract, *Chamomilla recutita* extract and *Rosmarinus officinalis* leaf extract.

3. The skincare composition according to claim 1, wherein the carbohydrate derivative is one or more selected from the group consisting of glycosylglycerol, xylitylglucoside, anhydroxylitol, fructose, and xylitol.

4. The skincare composition according to claim 1, wherein the thickener is one or more selected from the group consisting of lubrajel, cetostearyl alcohol, xanthan gum, and Carbomer.

5. The skincare composition according to claim 1, wherein the energy factor is one or more selected from the group consisting of artemia extract, palmitoyl tripeptide-1, palmitoyl tetrapeptide-7, and palmitoyl pentapeptide-4; the mass ratio of the energy factor to the carbohydrate derivative is (0.5-3):2.

6. The skincare composition according to claim 1, wherein the mass ratio of the red ginseng fermentation broth to the carbohydrate derivative to the complex plant extract is (1.3-2):(1-3.5):(0.2-0.5).

7. An essence lotion comprising the skincare composition according to claim 1.

* * * * *